(12) United States Patent
Boga et al.

(10) Patent No.: US 8,703,179 B2
(45) Date of Patent: Apr. 22, 2014

(54) MUCOSAL FORMULATION

(75) Inventors: RameshBabu Boga, Alpharetta, GA (US); Robert B. Johnson, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1349 days.

(21) Appl. No.: 11/302,992

(22) Filed: May 11, 2006

(65) Prior Publication Data

US 2007/0264206 A1    Nov. 15, 2007

(51) Int. Cl.
*A61K 9/127* (2006.01)
*A01N 57/26* (2006.01)
*A61K 31/685* (2006.01)
*A61K 31/565* (2006.01)

(52) U.S. Cl.
CPC ............ *A61K 31/685* (2013.01); *A61K 31/565* (2013.01); *A61K 9/127* (2013.01)
USPC .......................................... 424/450; 514/78

(58) Field of Classification Search
USPC ......................................................... 424/49
See application file for complete search history.

(56) References Cited

U.S. PATENT DOCUMENTS

| | | | |
|---|---|---|---|
| 4,326,052 A | 4/1982 | Kang et al. | |
| 4,326,053 A | 4/1982 | Kang et al. | |
| 4,377,636 A | 3/1983 | Kang et al. | |
| 4,385,123 A | 5/1983 | Kang et al. | |
| 4,563,366 A | 1/1986 | Baird et al. | |
| 4,737,323 A | 4/1988 | Martin et al. | |
| 5,190,927 A | 3/1993 | Chang et al. | |
| 5,288,499 A * | 2/1994 | Janoff et al. .................. | 424/450 |
| 5,616,341 A | 4/1997 | Mayer et al. | |
| 5,681,829 A | 10/1997 | Tempesta et al. | |
| 5,703,063 A * | 12/1997 | Chasalow ....................... | 514/78 |
| 5,744,158 A | 4/1998 | Mayer et al. | |
| 5,795,589 A | 8/1998 | Mayer et al. | |
| 5,891,465 A * | 4/1999 | Keller et al. .................. | 424/450 |
| 5,939,096 A | 8/1999 | Clerc et al. | |
| 6,083,530 A | 7/2000 | Mayer et al. | |
| 6,278,004 B1 | 8/2001 | Ghyczy | |
| 6,334,999 B1 | 1/2002 | Gilbert et al. | |
| 6,419,913 B1 | 7/2002 | Niemiec et al. | |
| 6,562,363 B1 * | 5/2003 | Mantelle et al. .............. | 424/434 |
| 6,567,693 B1 | 5/2003 | Allen | |
| 6,593,292 B1 | 7/2003 | Rothbard et al. | |
| 6,645,181 B1 | 11/2003 | Lavi et al. | |
| 2001/0006660 A1 * | 7/2001 | Lagace et al. .................. | 424/400 |
| 2001/0051656 A1 * | 12/2001 | Place et al. .................... | 514/530 |
| 2003/0100078 A1 | 5/2003 | Harding et al. | |
| 2003/0108597 A1 | 6/2003 | Chancellor et al. | |
| 2003/0171251 A1 * | 9/2003 | Pepys ............................. | 514/1 |
| 2003/0186897 A1 * | 10/2003 | Kozak et al. .................... | 514/23 |
| 2003/0204180 A1 | 10/2003 | Huang et al. | |
| 2004/0063787 A1 | 4/2004 | Villanueva et al. | |
| 2004/0097470 A1 | 5/2004 | Engel et al. | |
| 2004/0208921 A1 | 10/2004 | Ho et al. | |
| 2004/0242543 A1 | 12/2004 | Engel | |
| 2005/0095281 A1 | 5/2005 | Hofland et al. | |

FOREIGN PATENT DOCUMENTS

| | | | | |
|---|---|---|---|---|
| WO | 9937289 A1 | 7/1999 | | |
| WO | WO01/21174 A1 * | 9/2000 | ........... | A61K 31/337 |
| WO | 03028736 A2 | 4/2003 | | |
| WO | 03028736 A3 | 4/2003 | | |
| WO | WO03028736 * | 4/2003 | ............. | A61K 31/66 |
| WO | 2006042751 A2 | 4/2006 | | |

OTHER PUBLICATIONS

Baggott et al. NetBiochem, pp. 1-10, last modified on Jan. 5, 1995.*
Owen et al. "A Vaginal Fluid Stimulant", Contraception, 1999, p. 91.*
Lu et al., J. Nat. Prod., 1999, 62(6), pp. 824-828.*
Nash et al., Am. J. Obster. Gynecol., 1999, 181(6), pp. 1400-1406.*
Article—*A Vaginal Fluid Simulant*, Owen et al. *Contraception*, 59, pp. 91-99 (1999).
Article—"*Synthetic analogues of Irlbacholine, a novel antifungal plant metabolite isolated from Irlbachia Alata*", *Journal of Natural Products*, vol. 62, pp. 824-828 (1999).
Search Report and Written Opinion for PCT/US2006/046497, Apr. 25, 2007.

* cited by examiner

*Primary Examiner* — Brian Gulledge
(74) *Attorney, Agent, or Firm* — Dority & Manning, P.A.

(57) ABSTRACT

A mucosal formulation for administration to mucosal membranes, such as in the mouth, nasal passage, stomach, vagina, etc., is disclosed. The mucosal formulation contains a lipid-pharmaceutical agent complex formed from phospholipids possessing a hydrophobic moiety that orients into a hydrophobic phase and a polar head moiety that orients towards the aqueous phase (i.e., "amphipathic" lipids). When placed in an aqueous medium (e.g., vaginal fluid), the phospholipids form liposomes or other small lipid vesicles (e.g., micelles) that may then be used to deliver pharmaceutical agents into a living organism.

22 Claims, 8 Drawing Sheets

US 8,703,179 B2

MUCOSAL FORMULATION

BACKGROUND OF THE INVENTION

Post-menopausal women often suffer from a variety of problems associated with a marked reduction in endogenous estrogen production (from 120 pg/ml to around 18 pg/ml). When estrogen levels are low or absent, vascularity of the vagina is reduced and vaginal epithelium is thinned. The decrease in vascularity and vaginal epithelium results in less transudation and vaginal moisture. This may lead to vaginal atrophy, vaginal dryness, incontinence, etc. A decline in estrogen levels may also stem from other factors, such as oral contraceptive use, taking certain medications such as antihistamines, decongestants or antidepressants, intensive exercising, stress, cigarette smoking, frequent douching, and undergoing radiation or chemotherapy treatments. Regardless, estrogen is commonly administered orally, parenterally (e.g., by injection), or topically to increase mucous production and to provide vasodilatory effects. Unfortunately, estrogen-based therapies often result in an increase in moisture, which enhances the likelihood of yeast infection. Yeast infections are common mucus infections that include *candida* vaginitis, diaper dermatitis (or diaper rash), and oral infections. *Candida* is an opportunistic pathogen that colonizes to cause for infections. *Candida albicans*, for example, is present in most humans as a harmless commensal organism. Problems arise, however, when a person experiences a loss of normal bacterial flora. Although several antifungal agents are known to inhibit *Candida*, such as imidazole-based analogues, multiple therapies are nevertheless needed to treat both atrophic and yeast vaginitis. In addition, many antifungal agents have serious side effects.

As such, a need currently exists for a multi-functional mucosal formulation that is capable of delivering a pharmaceutical agent (e.g., estrogen) and also inhibiting the growth of microorganisms.

SUMMARY OF THE INVENTION

In accordance with one embodiment of the present invention, a method for promoting mucosal health is disclosed. The method comprises administering a mucosal formulation to a mucosal membrane (e.g., vaginal tissue). The mucosal formulation comprises a complex that includes a phospholipid and pharmaceutical agent. The phospholipid is formed from an alkyl phosphocholine.

In accordance with another embodiment of the present invention, a mucosal formulation is disclosed that comprises a vesicle. The vesicle includes a phospholipid and pharmaceutical agent. The phospholipid is formed from an alkyl phosphocholine having the following structure:

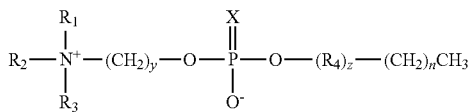

$R_1$, $R_2$, and $R_3$ are independently selected from the group consisting of hydrogen or $C_1$ to $C_6$ alkyl groups that are linear or branched, saturated or unsaturated, substituted or unsubstituted;

$R_4$ is selected from the group consisting of $C_1$ to $C_{40}$ alkyl groups that are linear or branched, saturated or unsaturated, substituted or unsubstituted;

X is O, S, or NH;
y is from 1 to 10;
z is from 0 to 40; and
n is from 4 to 24.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
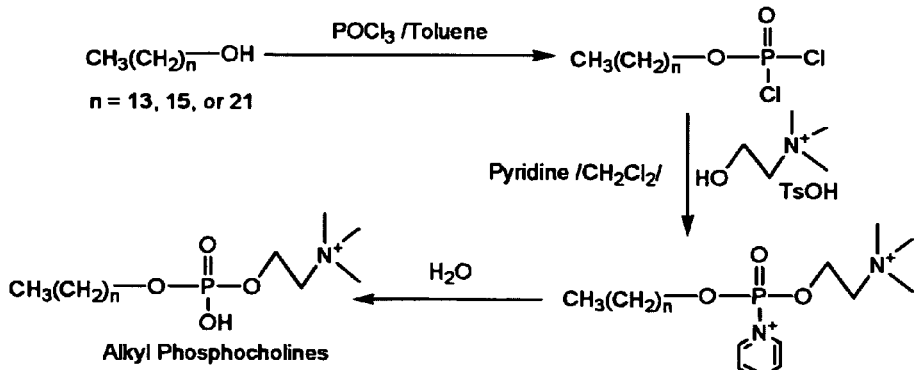
FIG. 1 is a diagram illustrating the alkyl phosphocholine synthesis technique used in Example 1.

Repeat use of references characters in the present specification and drawings is intended to represent same or analogous features or elements of the invention.

DETAILED DESCRIPTION OF REPRESENTATIVE EMBODIMENTS

Definitions

As used herein, the term "complex" generally refers to a mixture or aggregation that results from the reaction of components of the complex, such as by covalent bonds or non-covalent interactions (e.g., ionic interactions, hydrogen bonds, van der Waal interactions, hydrophobic interactions, etc.).

As used herein, the term "lipid-pharmaceutical agent complex" generally refers to a complex that contains a lipid component and a pharmaceutical agent component. Typically, such complexes are formed by the aggregation of lipid molecules and pharmaceutical agents in which the lipid component is a major component.

As used herein, the term "liposomes" generally refers to vesicles having a lipid bilayer separating an aqueous internal compartment from a bulk aqueous phase.

As used herein, the term "micelles" generally refers to vesicles having closed lipid monolayers with a fatty acid core and polar surface, or polar core with fatty acids on the surface.

As used herein, an "entrapped" pharmaceutical agent generally refers to an agent located in the aqueous volume of a lipid vesicle and/or an agent associated with the lipid.

As used herein, the term "pharmaceutical agent" generally includes molecules that are biologically, physiologically, or pharmacologically active and act locally or systemically in a patient or subject to treat a disease or condition, such as infection or inflammation. The term includes, without limitation, medicaments; vitamins; mineral supplements; substances used for the treatment, prevention, diagnosis, cure or mitigation of disease or illness; or substances that affect the structure or function of the body; or pro-drugs, which become biologically active or more active after they have been placed in a predetermined physiological environment. Exemplary pharmaceutical agents include, but are not limited to, antimicrobials, antibiotics, antimycobacterial, antifungals, antivirals, neoplastic agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergics, anticholinergics, anticancer agents, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, anti-obesity agents, antioxidants, vaso-active agents, bone-active agents, antiarthritics, hormones, hormone antagonists, and diagnostic agents. Numerous such compounds are known to those of skill in the art and described, for example, in *The Pharmacological Basis of Therapeutics*, Hardman, Limbird, Goodman & Gilman, McGraw-Hill, N.Y., (1996), as well as U.S. Pat. No. 6,419,913 to Niemiec, et al.; U.S. Pat. No. 6,562,363 to Mantelle, et al.; U.S. Pat. No. 6,593,292 to Rothbard, et al.; U.S. Pat. No. 6,567,693 to Allen, Jr.; and U.S. Pat. No. 6,645,181 to Lavi, et al., all of which are incorporated herein in their entirety by reference thereto for all purposes.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a mucosal formulation for administration to mucosal membranes, such as in the mouth, nasal passage, stomach, vagina, etc. In one particular embodiment, the mucosal formulation is used to promote vaginal health, particularly in post-menopausal females. The mucosal formulation contains a lipid-pharmaceutical agent complex formed from phospholipids possessing a hydrophobic moiety that orients into a hydrophobic phase and a polar head moiety that orients towards the aqueous phase (i.e., "amphipathic" lipids). When placed in an aqueous medium (e.g., vaginal fluid), the phospholipids form liposomes or other small lipid vesicles (e.g., micelles) that may then be used to deliver pharmaceutical agents into a living organism.

Any of a variety of pharmaceutical agents may be employed in the present invention. For instance, one particularly useful class of pharmaceutical agents for vaginal applications is non-androgenic steroids, such as progestins and estrogens. Suitable estrogens include synthetic and natural estrogens such as: estradiol (i.e., 1,3,5-estratriene-3,17-β-diol, or "17-β-estradiol") and its esters, including estradiol benzoate, valerate, cypionate, heptanoate, decanoate, acetate and diacetate; 17-α-estradiol; ethinylestradiol (i.e., 17-α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Suitable progestins include acetoxypregnenolone, allylestrenol, anagestone acetate, chlormadinone acetate, cyproterone, cyproterone acetate, desogestrel, dihydrogesterone, dimethisterone, ethisterone (17-α-ethinyltestosterone), ethynodiol diacetate, flu rogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. It is often desirable to co-administer a progestin along with an estrogen so that the estrogen is not "unopposed." Another exemplary class of pharmaceutical agents is anti-inflammatory agents that reduce pain, swelling, stiffness, inflammation, etc. For example, nonsteroidal anti-inflammatory drugs (NSAIDs) may be utilized, such as aspirin, ibuprofen, indomethacin, phenylbutazone, bromfenac, sulindac, nabumetone, ketorolac, mefenamic acid, and naproxen. Other suitable anti-inflammatory drugs are COX-2 inhibitors, such as celecoxib, meloxicam, rofecoxib, and flosulide. These drugs inhibit the production of the COX-2 (cyclooxygenase-2) enzyme induced by pro-inflammatory stimuli in migratory cells and inflamed tissue.

To form lipid vesicles in which the pharmaceutical agent is entrapped, for example, the pharmaceutical agent may be initially dissolved in an aqueous solvent, such as water or a biocompatible buffer solution (e.g., phosphate-buffered saline, HEPES, TRIS, etc.). Organic solvents may also be employed, such as dimethyl sulfoxide (DMSO), methanol, ethanol, propanol, propane glycol, butanol, isopropanol, pentanol, pentane, fluorocarbons (e.g., freon), ethers, etc. Surfactants may optionally be employed to aid in the dispersion of the agent within the solvent. The lipid is also dissolved in the solvent, either before, after, or in conjunction with the pharmaceutical agent. The pharmaceutical agent and lipid are typically mixed at a lipid-to-pharmaceutical agent molar ratio of about 3:1 to about 100:1 or higher, in some embodiments from about 3:1 to about 10:1, and in some embodiments, from about 5:1 to about 7:1.

Once dissolved in a solvent, the pharmaceutical agent and lipid may then be mixed using any known technique. One suitable technique includes sonication, such as with a probe or bath sonifier (e.g., Branson tip sonifier) at a controlled temperature as determined by the melting point of the lipid. Several examples of such sonication techniques are described in more detail in U.S. Pat. No. 4,737,323 to Martin, et al., which is incorporated herein in its entirety by reference thereto for all purposes. Homogenization is another method that relies on shearing energy to fragment large vesicles into smaller ones. In a typical homogenization procedure, multi-lamellar vesicles are recirculated through a standard emulsion homogenizer. Other suitable techniques may include vortexing, extrusion, microfluidization, homogenization, etc. Extrusion through a membrane (e.g., small-pore polycarbonate or an asymmetric ceramic) may also be used. Typically, a suspension is cycled through the membrane one or more times until the desired size distribution is achieved. The vesicles may be extruded through successively smaller-pore membranes to achieve a gradual reduction in size. Preferably, the vesicles have a size of about 0.05 microns to about 0.5 microns, and in some embodiments, from about 0.05 to about 0.2 microns. Other suitable methods for forming lipid vesicles may be described in U.S. Pat. No. 6,334,999 to Gilbert et al.; U.S. Pat. No. 6,083,530 to Mayer, et al.; U.S. Pat. No. 5,939,096 to Clerc, et al.; U.S. Pat. No. 5,795,589 to Mayer, et al.; U.S. Pat. No. 5,744,158 to Mayer, et al.; and U.S. Pat. No. 5,616,341 to Mayer et al., which are incorporated herein in their entirety by reference thereto for all purposes.

Once prepared, the vesicles may be dehydrated for longer storage. In one embodiment, the vesicles are loaded with the pharmaceutical agent as described above, dehydrated, and then rehydrated during use. For example, the vesicles may become rehydrated upon application to the vagina or prior to application. In alternative embodiments, however, the lipid vesicles may be formed without the pharmaceutical agent, dehydrated, and then rehydrated at or near the time of use with a solution of the pharmaceutical agent. In either case, the vesicles are preferably dehydrated under reduced pressure using standard freeze-drying equipment or equivalent apparatus. The lipid vesicles and their surrounding medium may also be frozen in liquid nitrogen before dehydration and then placed under reduced pressure. Upon dehydration, the lipid vesicles may be stored for extended periods of time until they are to be used. The appropriate temperature for storage will depend on the make up of the lipid vesicles and the temperature sensitivity of the encapsulated pharmaceutical agent. For example, dehydrated lipid vesicles containing heat labile pharmaceutical agents are typically stored under refrigerated conditions so that the potency of the agent is not lost. Also, for such agents, the dehydration process may be carried out at reduced temperatures rather than at room temperature.

The dosage of the pharmaceutical agent will generally vary depending on the subject being treated, the severity of the condition, the judgment of the prescribing physician, etc. The entire dosage of the pharmaceutical agent may be made biologically available upon application. Alternatively, the pharmaceutical agent may be controllably or sustainably delivered. For example, upon contact with body fluids including blood, tissue fluid, lymph, etc., the lipid vesicle may fuse with other bilayers (e.g., the cell membrane) to deliver the pharmaceutical agent for a sustained or extended period (as compared to the release from a bolus). This release may result in prolonged delivery of therapeutically effective amounts of the incorporated pharmaceutical agent. Such a system may result in prolonged delivery of the pharmaceutical agent, such as from about 2 to about 240 hours, and in some embodiments from about 4 to about 120 hours.

Besides being capable of delivering a pharmaceutical agent, the present inventors have also discovered that certain lipid vesicles are also capable of providing selective inhibition for the growth of microorganisms, such as bacteria, yeast, fungi, mold, protozoa, viruses, etc. For example, the lipid vesicles may inhibit the growth of *Candida* microorganisms commonly associated with yeast infection (e.g., vaginal infection, diaper rash, etc.), such as *Candida albicans*. In addition, the present inventors have also found that the growth of other microorganisms may be inhibited, such as *Staphyloccus aureus* and *Gardnerella vaginate*. Treatment with the vaginal formulation may, for example, provide a log reduction for *Candida albicans, Staphylococcus aureus*, and/or and *Gardnerella vaginale* of at least about 2, in some embodiments at least about 3, in some embodiments at least about 4, and in some embodiments, at least about 5 (e.g., about 6). Log reduction, for example, may be determined from the % population killed by the formulation according to the following correlations:

| % Reduction | Log Reduction |
|---|---|
| 90 | 1 |
| 99 | 2 |
| 99.9 | 3 |
| 99.99 | 4 |
| 99.999 | 5 |
| 99.9999 | 6 |

One particularly effective class of lipid vesicles capable of providing the desired antimicrobial efficacy includes alkyl phosphocholines having the following structure:

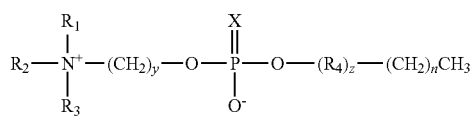

$R_1$, $R_2$, and $R_3$ are independently selected from the group consisting of hydrogen, a linear or branched $C_1$ to $C_6$ alkyl group (e.g., ethyl or methyl), which may be saturated or unsaturated and unsubstituted or optionally substituted at the same or at different carbon atoms with one, two or more halogen, nitro, cyano, hydroxy, $C_1$ to $C_6$ alkoxy, amino, mono-($C_1$ to $C_4$) alkylamino or di($C_1$ to $C_4$) alkylamino groups;

$R_4$ is selected from the group consisting of linear or branched $C_1$ to $C_{40}$ alkyl groups, which may be saturated or unsaturated and unsubstituted or optionally substituted at the same or at different carbon atoms with one, two or more halogen, nitro, cyano, hydroxy, $C_1$ to $C_{24}$ alkoxy, amino, mono-($C_1$ to $C_{24}$) alkylamino or di($C_1$ to $C_{24}$) alkylamino groups;

X is O, S, or NH;

y is from 1 to 10, such as from 2 to 4;

z is from 0 to 40; and n is from 1 to 40, such as from 4 to 24.

Particular examples of suitable zwitterionic phospholipids having the general formula set forth above include, without limitation, hexadecyl thiophosphocholine, tetradecyl phosphocholine, hexadecyl phosphocholine, docosanoyl phosphocholine, 1,2-dihexadecyl-rac-glycero-3-phosphocholine, and DL-α-lysophosphatidylcholine-r-o-hexadecyl.

Regardless of the particular structure selected, the phospholipids employed in the present invention are zwitterionic in that they contain positively and negatively charged groups in the same molecule. Due to its polarity, the zwitterionic molecule possesses an affinity for water and is thus hydrophilic. The long chain carbon group (e.g., $(CH_2)_nCH_3$) of the alkylphosphocholine derivatives also enhances the ability of the molecule to form vesicles that hold more water molecules. The present inventors have discovered that such hydrophilic phospholipids may effectively act as moisturizers for mucosal membranes, while simultaneously delivering a pharmaceutical agent and inhibiting the growth of microorganisms.

The phospholipid is employed in the mucosal formulation in an effective amount to achieve the desired level of treatment. An "effective amount" is an amount sufficient to inactivate, but not necessarily kill, pathogenic microorganisms. In fact, when used in vaginal applications, it may be desired to use a concentration that does not significantly affect or inhibit the growth characteristics of the normal vaginal flora (e.g., *Lactobacillus acidophilus* or "lactobacilli") or otherwise significantly irritate the vaginal tissue when used at inhibitory, noncytotoxic, or clinical concentrations. For example, the phospholipid may be employed at a concentration of about 0.01 to about 1000 micrograms per milliliter (μg/ml), in some embodiments from about 0.1 μg/ml to about 100 μg/ml, in some embodiments from about 0.2 μg/ml to about 10 μg/ml, and in some embodiments, from about 0.5 μg/ml to about 5 μg/ml. It should be understood that the concentration may vary with the age, condition, and type of infection suffered by the patient, and may be readily determined by one of skill in the art.

Pharmaceutically acceptable excipients may also be employed in the present invention. For example, to ensure that the vesicles survive dehydration without losing a substantial portion of their internal contents, one or more protective sugars may be employed to interact with the lipid vesicle membranes and keep them intact as the water in the system is removed. A variety of sugars may be used, such as trehalose, maltose, sucrose, glucose, lactose, and dextran, streptomycin, and dihydrostreptomycin. The sugars are typically included as part of either the internal or external media of the lipid vesicles. Most preferably, the sugars are included in both the internal and external media so that they can interact with both the inside and outside surfaces of the vesicle membranes. Inclusion in the internal medium is accomplished by adding the sugar or sugars to the buffer that becomes encapsulated in the lipid vesicles during the lipid vesicle formation process. Because in most cases this buffer also forms the bathing medium for the finished lipid vesicles, inclusion of the sugars in the buffer also makes them part of the external medium. Of course, if an external medium other than the original buffer is used, e.g., to create a transmembrane potential, the new external medium may also include one or more of the protective sugars.

In addition, to help avoid adverse physiological effects, the mucosal formulation may also be "isotonic" in that it has an osmolarity that is substantially similar to mucosa (i.e., about 290 milliosmoles per liter ("mOsm/L")). For example, an isotonic formulation may have an osmolarity of from about 270 to about 310 mOsm/L, in some embodiments from about 280 to about 300 mOsm/L, and in one embodiment, about 290 mOsm/L. The osmolarity of the formulation may be estimated using the following equation:

$$O_{formulation} = \Sigma O_{species}$$

wherein, $O_{species}$ is the osmolarity of a species in the formulation. The osmolarity of a particular species is likewise determined using the following equation:

$$O_{species} = [c/m] \times n \times \phi \times 1000$$

wherein, c is the concentration of the species, in grams per liter;

m is the average molecular weight of the species;

n is the number of particles that dissociate from the molecule;

φ is the osmotic coefficient of the species.

If desired, a tonicity agent may be employed in some embodiments of the present invention to help achieve the desired osmolarity. Suitable tonicity agents may include ionic salts, such as sodium chloride, potassium chloride, and calcium chloride; nonionic agents, such as dextrose, glycerin, propylene glycol, mannitol, sorbitol, xylitol, trehalose, and sucrose; and so forth. When utilized, any effective amount of the tonicity agent(s) may be employed in the mucosal formulation to achieve the desired osmolarity. For example, the tonicity agent(s) may be present in an amount from about 0.01 wt/vol % to about 5 wt/vol %, in some embodiments from about 0.05 wt/vol % to about 2 wt/vol %, and in some embodiments, from about 0.1 wt/vol % to about 1 wt/vol % of the mucosal formulation. As used herein, the designation "wt/vol %" refers to the value obtained by dividing the weight of a substance (in grams) by the volume of the solution (in milliliters), and then multiplying by 100.

The pH of the mucosal formulation may also be controlled within a range that is considered biocompatible. For instance, the pH may be maintained at a mildly acidic level when used in vaginal applications. The pH may be within a range of from about 2.5 to about 5.5, in some embodiments from about 2.5 to about 5.0, and in some embodiments, from about 3.0 to about 4.5. Various pH modifiers may be utilized to achieve the desired pH level. Some examples of pH modifiers that may be used in the present invention include, but are not limited to, mineral acids, sulfonic acids (e.g., 2-[N-morpholino] ethane sulfonic acid), carboxylic acids, and polymeric acids. Specific examples of suitable mineral acids are hydrochloric acid, nitric acid, phosphoric acid, and sulfuric acid. Specific examples of suitable carboxylic acids are lactic acid, acetic acid, citric acid, glycolic acid, maleic acid, gailic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid. Basic pH modifiers may also be used in some embodiments of the present invention to provide a higher pH value. Suitable pH modifiers may include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine. When utilized, the pH modifier may be present in any effective amount needed to achieve the desired pH level. In some embodiments, the pH modifier(s) are present in an amount between about 0.001 wt/vol % to about 5 wt/vol %, in some embodiments between about 0.005 wt/vol % to about 1 wt/vol %, and in some embodiments, between about 0.01 wt/vol % to about 0.25 wt/vol % of the formulation.

Besides the ingredients mentioned above, the mucosal formulation may also contain a preservative or preservative system to inhibit the growth of microorganisms over an extended period of time. Suitable preservatives for use in the present formulation may include, for instance, alkanols, disodium EDTA (ethylenediamine tetraacetate), EDTA salts, EDTA fatty acid conjugates, isothiazolinone, benzoic esters (parabens) (e.g., methylparaben, propylparaben, butylparaben, ethylparaben, isopropylparaben, isobutylparaben, benzylparaben, sodium methylparaben, and sodium propylparaben), benzoic acid, propylene glycols, sorbates, urea derivatives (e.g., diazolindinyl urea), and so forth. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate). Another suitable preservative is Kathon CG®, which is a mixture of methylchloroisothiazolinone and methylisothiazolinone available from Rohm & Haas; Mackstat H 66 (available from Mcintyre Group, Chicago, Ill.). Still another suitable preservative system is a combination of 56% propylene glycol, 30% diazolidinyl urea, 11% methylparaben, and 3% propylparaben available under the name GERMABEN® II from International Specialty Products of Wayne, N.J. The amount of the preservative or preservative system utilized may vary depending on the relative amounts of the other components present within the formulation. For example, in some embodiments, preservative(s) are present in the formulation in an amount from about 0.001 wt/vol % to about 5 wt/vol %, in some embodiments from about 0.001 wt/vol % to about 1 wt/vol %, and in some embodiments, from about 0.1 wt/vol % to about 0.15 wt/vol % of the formulation.

Any method of administering the mucosal formulation may be employed in the present invention. For example, the formulation may be topically applied to vaginal mucosa in the form of a douche formulation, spray, moisturizer, lotion, cream, jelly, liniment, ointment, salve, oil, foam, gel, film, wash, suppository, slow-releasing polymer, coating, liquid, capsule, tablet, film, sponge, ovule, etc. The lipid vesicles may also be applied to an insert, tampon, wipe or pad, incontinent device, etc. for subsequent vaginal administration. In one particular embodiment, a vaginal formulation is topically applied in the form of a gel. A "gel" is a colloid in which a disperse phase combines with a dispersion medium to produce a jelly-like, solid or semi-solid material. The gel may form in less than about 1 hour, in some embodiments less than about 1 minute, and in some embodiments, less than about 30 seconds. Such rapid gelation reduces the likelihood of leakage during use. In addition, because the gel may form intravaginally, it is more likely to retain its structure and shape over an extended period of time. In this manner, the gel may provide the prolonged release of the pharmaceutical agent. For instance, the gel may remain within the vagina for about 2 to about 48 hours to provide the desired effect.

Although a variety of compounds may be employed, water is usually employed as the dispersion medium for the gel to optimize biocompatibility. Other possible dispersion mediums include non-aqueous solvents, including glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Typically, the dispersion medium (e.g., water) constitutes greater than about 75 wt/vol %, in some embodiments greater than about 90 wt/vol %, and in some embodiments, from about 95 wt/vol % to about 99 wt/vol % of the mucosal formulation.

The disperse phase of the gel may be formed from any of a variety of different gelling agents, including temperature responsive ("thermogelling") compounds, ion responsive compounds, and so forth. Thermogelling systems, for instance, respond to a change in temperature (e.g., increase in temperature) by changing from a liquid to a gel. Generally speaking, the temperature range of interest is from about 25° C. and 40° C., in some embodiments from about 35° C. and 39° C., and in one particular embodiment, at the human body temperature (about 37° C.). Compositions that change state at about this temperature are useful because they will remain in a body cavity, for example, after they have been delivered. Any of a variety of thermogelling compounds that are capable of gelling may be used in the present invention. In some cases, thermogelling block copolymers, graft copolymers, and/or homopolymers may be employed. For example, polyoxyalkylene block copolymers may be used in some embodiments of the present invention to form a thermo-gelling composition. The term "polyoxyalkylene block copolymers" refers to copolymers of alkylene oxides, such as ethylene oxide and propylene oxide, which form a gel when dispersed in water in a sufficient concentration. Some suitable polyoxyalkylene block copolymers include polyoxybutylene block copolymers and polyoxyethylene/polyoxypropylene block copolymers ("EO/PO" block copolymers), such as described in U.S. Patent Application Publication No. 2003/0204180 to Huang, et al., which is incorporated herein in its entirety by reference thereto for all purposes. For instance, exemplary polyoxyalkylene block copolymers include polyoxyethyl ene/polyoxypropylene block copolymers (EO/PO block copolymers) having the following general formula:

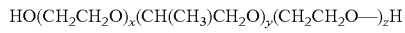

wherein, x, y, and z are each integers in the range of about 10 to about 150.

The polyoxyethylene chain of such block copolymers typically constitutes at least about 60 wt. %, in some embodiments at least about 70 wt. % of the copolymer. Further, the copolymer typically has a total average molecular weight of at least about 5000, in some embodiments at least about 10,000, and in some embodiments, at least about 15,000. Suitable EO/PO polymers for use in the mucosal formulation of the present invention are commercially available under the trade name PLURONIC® (e.g., F-127 L-122, L-92, L-81, and L-61) from BASF Corporation, Mount Olive, N.J.

Of course, other thermogelling compounds may also be used in the present invention. For example, other suitable thermogelling polymers may include homopolymers, such as poly(N-methyl-N-n-propylacrylamide), poly(N-n-propylacrylamide), poly(N-methyl-N-isopropylacrylamide), poly(N-n-propylmethacrylamide), poly(N-isopropylacrylamide), poly(N,n-diethylacrylamide); poly(N-isopropylmethacrylamide), poly(N-cyclopropylacrylamide), poly(N-ethylmethacrylamide), poly(N-methyl-N-ethylacrylamide), poly(N-cyclopropylmethacrylamide), and poly(N-ethylacrylamide). Still other examples of suitable thermogelling polymers may include cellulose ether derivatives, such as hydroxypropyl cellulose, methyl cellulose, hydroxypropylmethyl cellulose, and ethylhydroxyethyl cellulose. Moreover thermogelling polymers may be made by preparing copolymers between (among) monomers, or by combining such homopolymers with other water-soluble polymers, such as acrylic monomers (e.g., acrylic or methacrylic acid, acrylate or methacrylate, acrylamide or methacrylamide, and derivatives thereof).

Ion responsive compounds are also suitable for use in the present invention. Such compounds are generally well known in the art, and tend to form a gel in the presence of certain ions or at a certain pH. For instance, one suitable class of ion responsive compounds that may be employed in the present invention is anionic polysaccharides. Anionic polysaccharides may form a three-dimensional polymer network that functions as the disperse phase of the gel. Generally speaking, anionic polysaccharides include polysaccharides having an overall anionic charge, as well as neutral polysaccharides that contain anionic functional groups.

It is well known that vaginal mucosa contains certain monovalent and polyvalent cations, such as sodium ($Na^+$) and calcium ($Ca^{2+}$) ions. See e.g., Owen, D. H. and Katz, D. F., A Vaginal Fluid Simulant, *Contraception*, 59, 91-95 (1999). Thus, such cations may be used to crosslink anionic polysaccharide molecules to form a three-dimensional network, i.e., a gel. The ability to form a gel based on the reaction with ions contained in vaginal mucosa provides a variety of benefits to the vaginal formulation. For example, due to their high molecular weight, most anionic polysaccharides will not be absorbed by the body such that their gel-like properties may be maintained while in the vagina. Still another benefit of saccharide-based gels is that they are generally biocompatible and biodegradable. Further, unlike compositions in which gel formation is induced by temperature (i.e., thermogels), the vaginal formulation of the present invention may be stored and transported at a variety of different temperatures without fear of premature gelation. It should be understood, however, that the formulation may be partially or wholly gelled prior to application to the vagina in other embodiments of the present invention.

Any of a variety of anionic polysaccharides capable of forming a gel when contacted with vaginal mucosa may be used in the present invention. Such gel-forming anionic polysaccharides are typically stable over the normal acidic pH values found in the vagina (e.g., from about 2.5 to about 5.5). For instance, some suitable examples of gel-forming anionic polysaccharides include natural gums, such as gellan gum and alginate gums (e.g., ammonium and alkali metal of salts of alginic acid); chitosan; carboxymethylcellulose, pectins, carrageenan, xantham gum, and derivatives or salts thereof. The particular type of anionic polysaccharide selected will depend, in part, on the nature of the vaginal formulation and the other components used therein. For example, carrageenan is sensitive to particular types of cations, e.g., it typically gels in the presence of potassium but not sodium. Glycuronans, likewise, typically gel in the presence of divalent cations (e.g., $Ca^{2+}$), but not monovalent cations (e.g., $Na^+$). Xanthan gum may gel in the presence of divalent cations, but only at a relatively high pH.

Although any of the above-described anionic polysaccharides may be used in the present invention, gellan gum is particularly desired, either alone or in combination with other gelling agents, because it is able to form a gel in the presence of a wide variety of different cations, including both monovalent and divalent cations. Gellan gum is produced from strains of the bacteria, *Sphingomonas Elodea*. Typically, the gum is produced as an extracellular product through the aqueous cultivation of the microorganisms in a medium containing appropriate carbon, organic and inorganic nitrogen, and phosphate sources. The fermentation is carried out under sterile conditions with strict control of aeration, agitation, temperature, and pH. When fermentation is complete, the resulting viscous broth is pasteurized to kill viable cells prior to recovery of the gum. The gum may be recovered in a variety of ways. For instance, direct recovery from the broth yields the gum in its native or "high acyl" form. On the other hand, recovery after deacylation (e.g., by treatment with a base) yields the gum in its "low acyl" form. The degree of deacylation (i.e., the percentage of acyl groups removed) may be controlled by varying the temperature (e.g., 25° C. to 85° C.), the amount of base (e.g., pH>7.0), the reaction time, etc. Regardless, the constituent sugars of gellan gum are glucose, glucuronic acid and rhamnose in the molar ratio of about 2:1:1. These sugars are linked together to give a primary structure having a linear tetrasaccharide repeat unit.

The gellan gum may be either high or low acyl gellan. In the high acyl (or "native") form, two acyl substituents, acetate and glycerate, are present. Both substituents are located on the same glucose residue and, on average, there is one glycerate per repeat unit and one acetate per every two repeat units. In the low acyl form, the acyl groups may be wholly or partially removed through deacylation. The degree of deacylation of deacylated gellan gums may be at least about 20%, in some embodiments at least about 50%, and in some embodiments, at least about 75%. Alternatively, the low acyl gellan gum may simply be "nonacylated" in that it is formed without acyl groups by genetically engineered bacteria. Regardless of the manner in which they are formed, low acyl gellan gums generally have a gelation temperature within the range 30° C. to 50° C. depending on the nature and concentration of the cations present. In contrast, most high acyl gellan gums have a gelation temperature of above 50° C. For this reason, a low acyl gellan gum may be desired so that it may gel at body temperatures of about 37° C., but remain stable at typical storage and transportation temperatures of about 25° C. In addition, low acyl gellan gums are also firm and elastic, and thus may retain their shape after delivery to the vaginal cavity.

Of course, other types of gellan gums may also be used in the present invention. In fact, the term "gellan gum" is intended to encompass any form of gellan, including native gellan, clarified gellan, deacylated gellan, nonacylated gellan (e.g., produced from genetically engineered bacteria), clarified gellan (the polysaccharide is fully or partially removed from the bacterial debris), chemically modified gellan, etc. Various types of gellan gums and methods for forming such gums are described in U.S. Pat. Nos. 4,326,052; 4,326,053 to Kang, et al.; U.S. Pat. Nos. 4,377,636; 4,385,123; 4,563,366 to Baird, et al.; U.S. Pat. No. 5,190,927 to Chang, et al.; as well as U.S. Patent Application Publication No. 2003/0100078 to Herding, et al., all of which are incorporated herein in their entirety by reference thereto for all purposes. Gellan gums are commercially available from a variety of different sources. For example, GELRITE™ gellan gum is available from Sigma-Aldrich Chemical Co. of St. Louis, Mo., and is produced from a naturally occurring polysaccharide after deacylation and clarification. Deacylated gellan is also available from CP Kelco U.S., Inc. of Chicago, Ill. under the name KELCOGEL®.

Regardless of the type selected, the gelling agent(s) are generally present in the vaginal formulation in an amount sufficient to form a self-supporting gel. This amount may vary depending on a variety of factors, such as the nature of the gelling agent(s), the conditions of intended use, the nature of other components in the vaginal formulation, and so forth. In most embodiments, however, the gelling agent(s) are present in an amount of from about 0.01 wt/vol % to about 10 wt/vol %, in some embodiments from about 0.05 wt/vol % to about 5 wt/vol %, and in some embodiments, from about 0.1 wt/vol % to about 1 wt/vol % of the vaginal formulation.

A gelling formulation may be provided in any desired form (e.g., liquid, powder, etc). In fact, one particular benefit of the formulation is that it may be administered as a liquid, which allows for the selection of a wider variety of administration techniques than would otherwise be available for a solid or semi-solid gel. One technique that may be employed includes dispensing the formulation through a liquid applicator, such as a syringe or tube, into the vaginal cavity. The administered volume of the formulation may constitute a single dose or two or more doses. Although not necessarily required, the vaginal formulation of may also be sterilized prior to administration. Sterilization may be accomplished by any technique known in the art, such as using a gas (e.g., ethylene oxide), radiation (e.g., gamma), or heat (autoclaving). If desired, the formulation may be subjected to one or more filtration steps prior to sterilization to help remove contaminants.

The present invention may be better understood with reference to the following examples.

EXAMPLE 1

Figure 2:
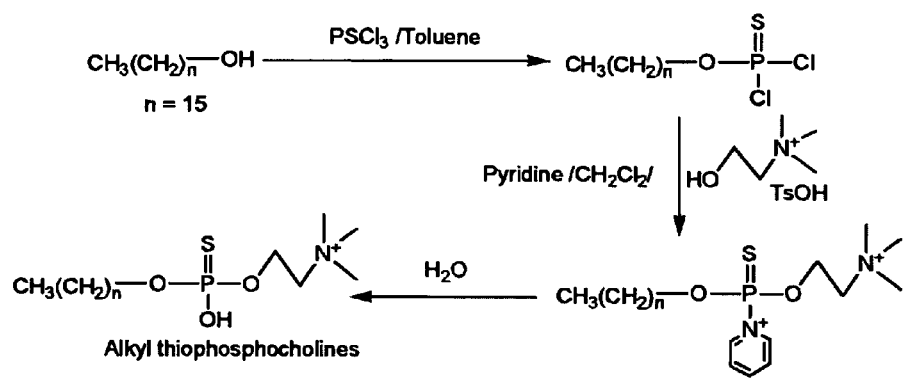
FIG. 2 is a diagram illustrating the alkyl thiophosphocholine synthesis technique used in Example 1.

Various phosphocholine derivatives were synthesized using a three-step process as shown in FIGS. 1-2. Specifically, 0.484 grams of hexadecanol (n=15) (from Aldrich Chemical Company) was mixed with 20 milliliters of toluene and 100 milliliters of phosphoryl chloride ("$POCl_3$"). The mixture was heated in an oil bath at 87 to 90° C. for 5 hours. After cooling to room temperature, the reaction mixture was concentrated in vacuum. 50 milliliters of methylene chloride and 1.38 grams of choline tosylate were then stirred into the mixture at room temperature for 40 to 50 hours. This reaction mixture was concentrated by a rotavaporator and the resulting residue was mixed with 1.5 milliliters of water. The residue was stirred at room temperature for 5 hours and concentrated with a nitrogen stream to give crude hexadecyl phosphocholine. Tetradecyl phosphocholine ($C_{14}$ chain) and docosanoyl phosphocholine ($C_{22}$ chain) were also synthesized using the technique described above, except that tetradecanol (n=13) and docosanoyl alcohol (n=21) were used to as starting materials instead of hexadecanol. Further, as shown in FIG. 2, the procedure set forth above was also used to synthesize hexadecyl thiophosphocholine, except that thiophosphoryl chloride was used instead of phosphoryl chloride. The expected molecular ion and the corresponding mass spectral results for each synthesized phosphocholine or thiophosphocholine derivatives were determined using mass spectral analysis. The results are shown below in Table 1.

TABLE 1

Mass Spectrometry Characterization

| Code | Structure | Exact mass | Confirmatory data from MS |
|---|---|---|---|
| BRB-1 | $C_{21}H_{46}NO_4P$ (Hexadecyl phosphocholine) | 407.316 | $[M + H]^+$ at 408.4<br>$[M + H + M]^+$ at 815.5 (dimer)<br>MS/MS of 408.4 → 125, 184<br>MS/MS of 815.5 → 408<br>Isotope pattern consistent with theoretical formula. |
| BRB-2 | $C_{27}H_{58}NO_4P$ (Docosanoyl phosphocholine) | 491.410 | $[M + H]^+$ at 492.6 (very weak)<br>$[M + H + M]^+$ at 983.8 (dimer)<br>MS/MS of 492.6 → 184<br>MS/MS of 983.8 → 492.4<br>Isotope pattern consistent with theoretical formula. |
| BRB-3 | $C_{19}H_{42}NO_4P$ (Tetradecyl phosphocholine) | 379.285 | $[M + H]^+$ at 380.6<br>$[M + H + M]^+$ at 760.7 (dimer)<br>MS/MS of 492.6 → 125, 184<br>MS/MS of 760.7 → 380.3<br>Isotope pattern consistent with theoretical formula. |

TABLE 1-continued

Mass Spectrometry Characterization

| Code | Structure | Exact mass | Confirmatory data from MS |
|---|---|---|---|
| BRB-4 | (structure shown) C$_{21}$H$_{46}$NO$_3$PS (Hexadecyl thiophosphocholine) | 423.294 | [M + H]$^+$ at 424.6 (very weak) 408.4 ion may be BRB-1 MS/MS of 424.6 → 141, 182 Isotope pattern consistent with theoretical formula. |

EXAMPLE 2

Figure 3:
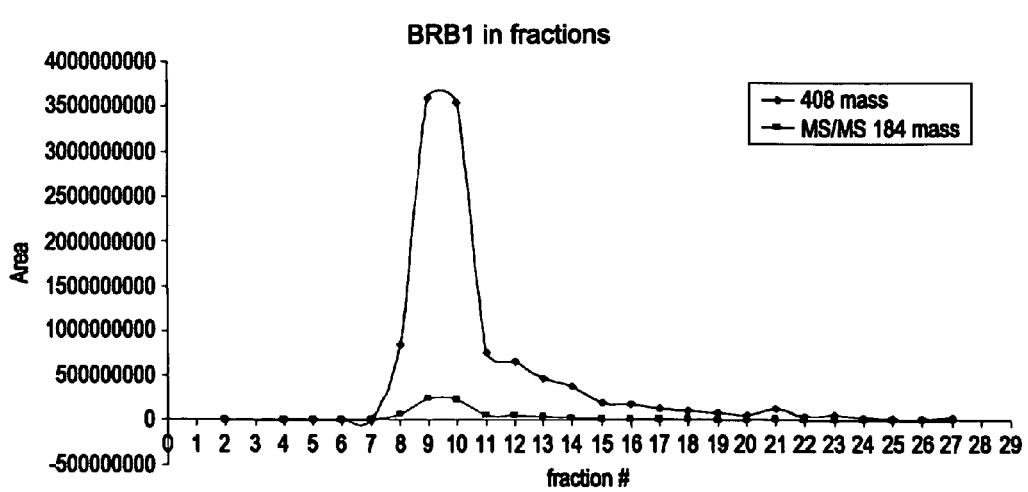
FIG. 3 is a graphical depiction of hexadecylphosphocholine ("BRB1") fractions from the LC/MS traces of Example 2 in which the total area is plotted versus the fraction number.
Figure 4:
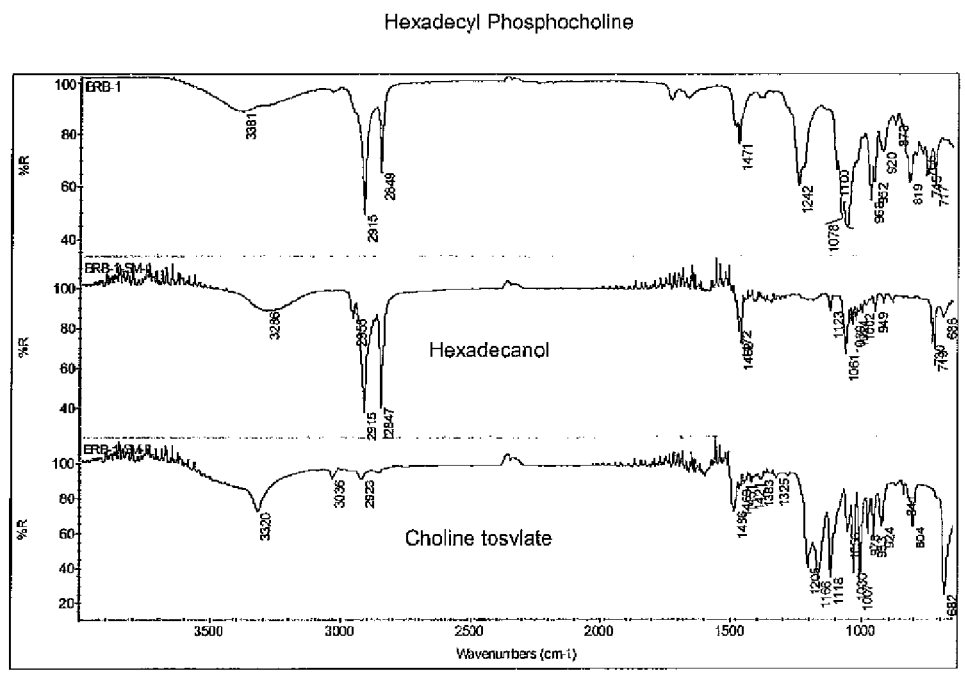
FIG. 4 is the infrared spectra of hexadecyl phosphocholine ("BRB1") in comparison to the hexadecanol ("BRB-SM-1") and choline tosylate ("BRB-SM-2") starting materials of Example 2.
Figure 5:
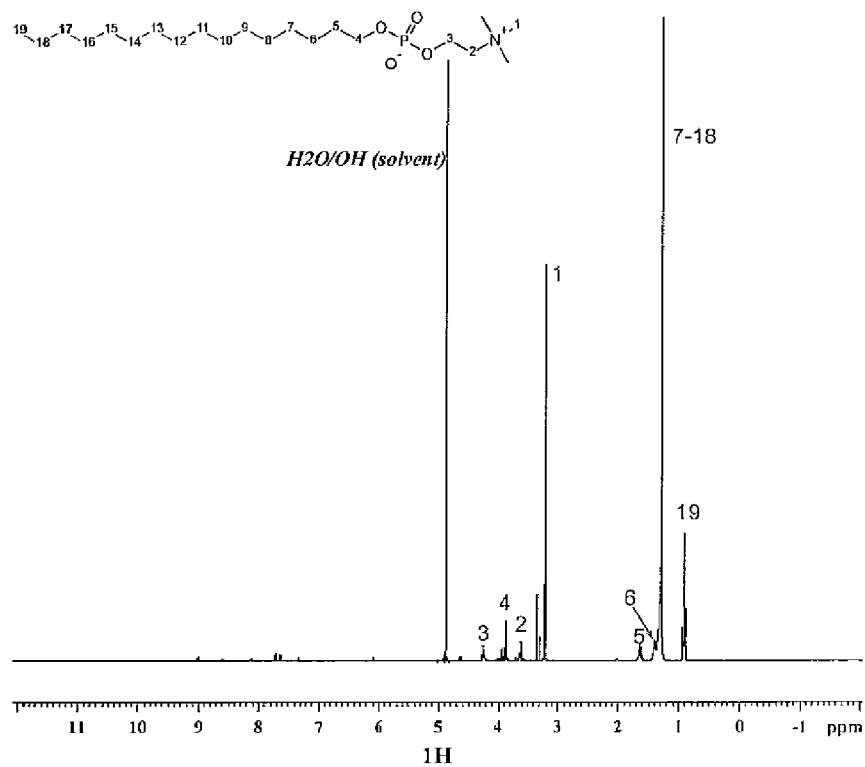
FIG. 5 is the proton NMR of hexadecyl phosphocholine ("BRB-1") of Example 2.
Figure 6:
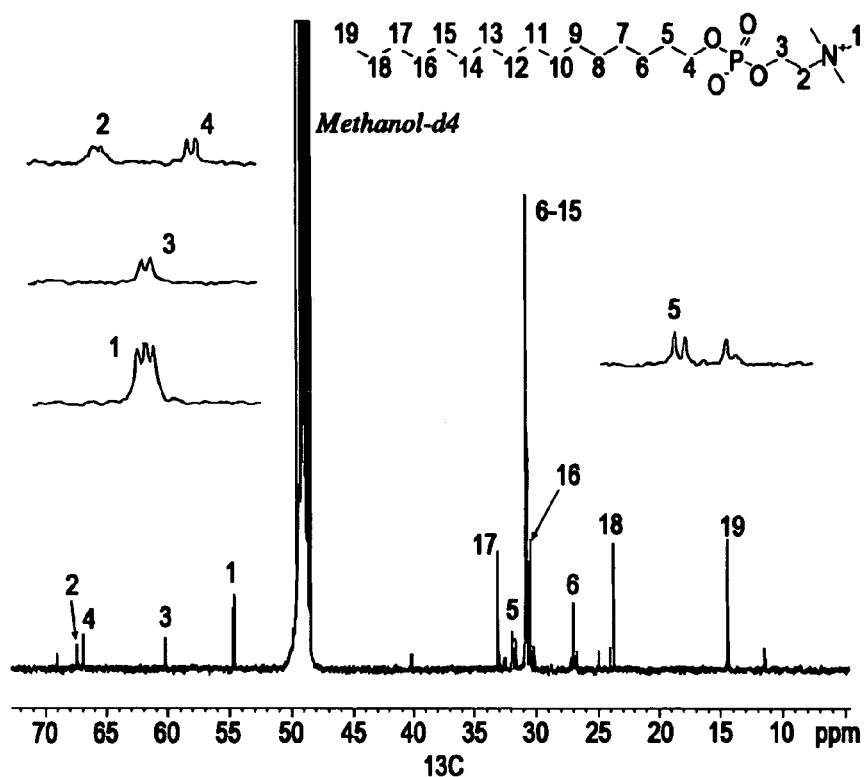
FIG. 6 is the carbon-13 NMR of hexadecyl phosphocholine ("BRB-1") of Example 2.
Figure 7:
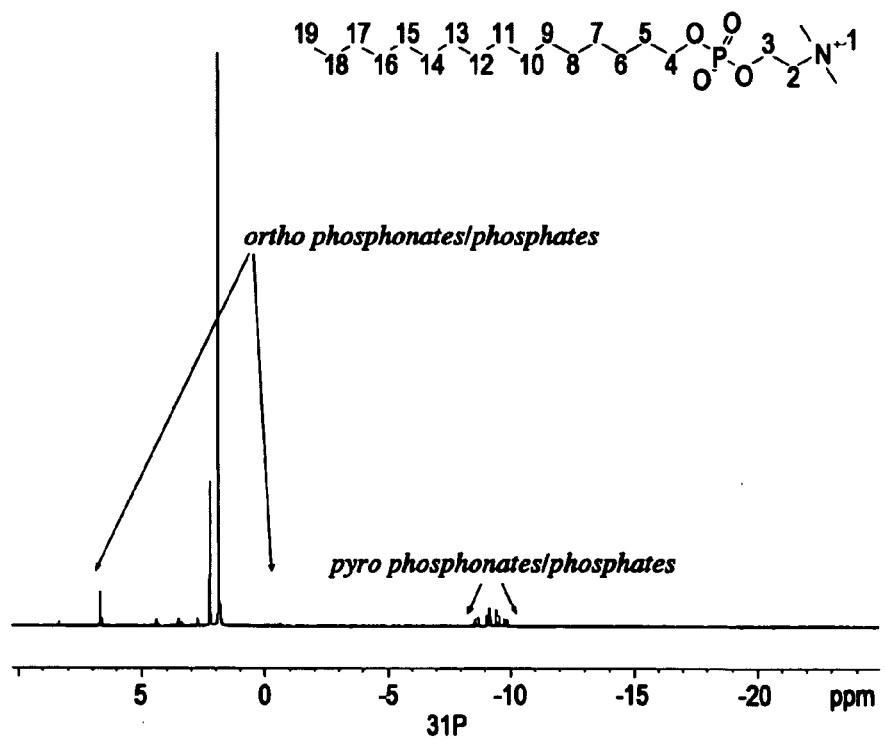
FIG. 7 is the phosphorus-31 NMR of hexadecyl phosphocholine ("BRB-1") of Example 2.
Figure 8:
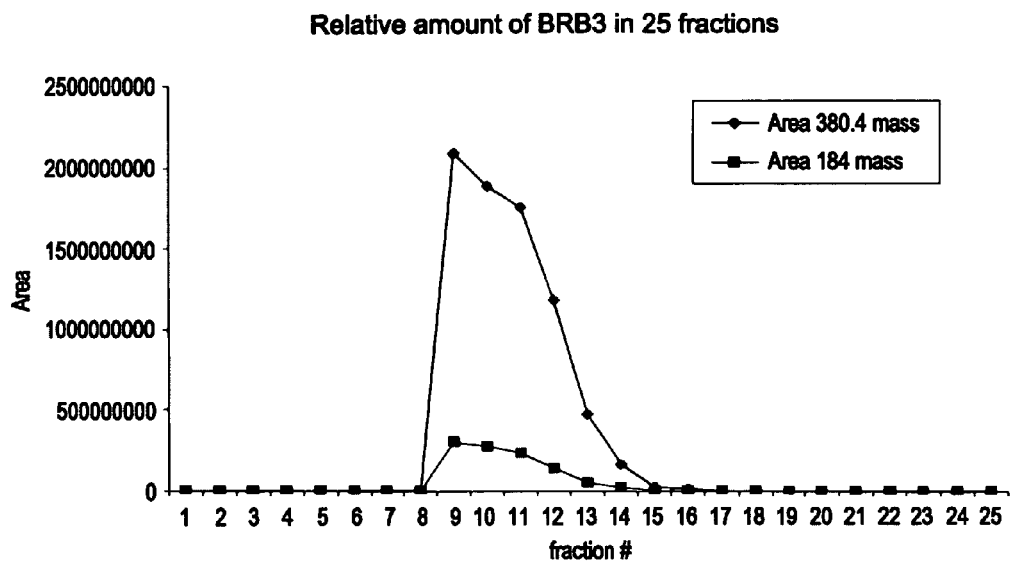
FIG. 8 is a graphical depiction of the tetradecyl phosphocholine ("BRB-3") fractions from the LC/MS traces of Example 2 in which the total area is plotted versus the fraction number.
Figure 9:
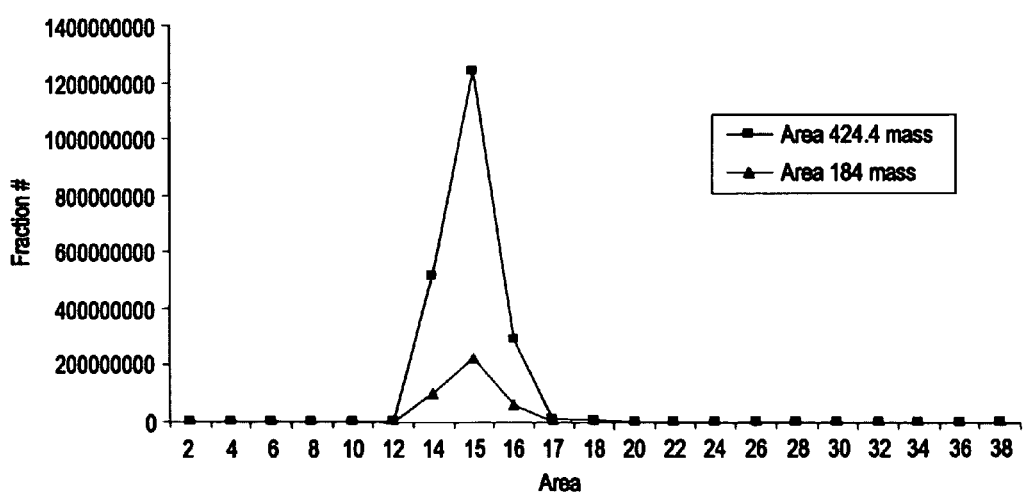
FIG. 9 illustrates the relative amounts of hexadecyl thiophosphocholine ("BRB-4") [M$^+$ 424] in column fractions of Example 2 in which the fraction number is plotted versus total area.
Figure 10:
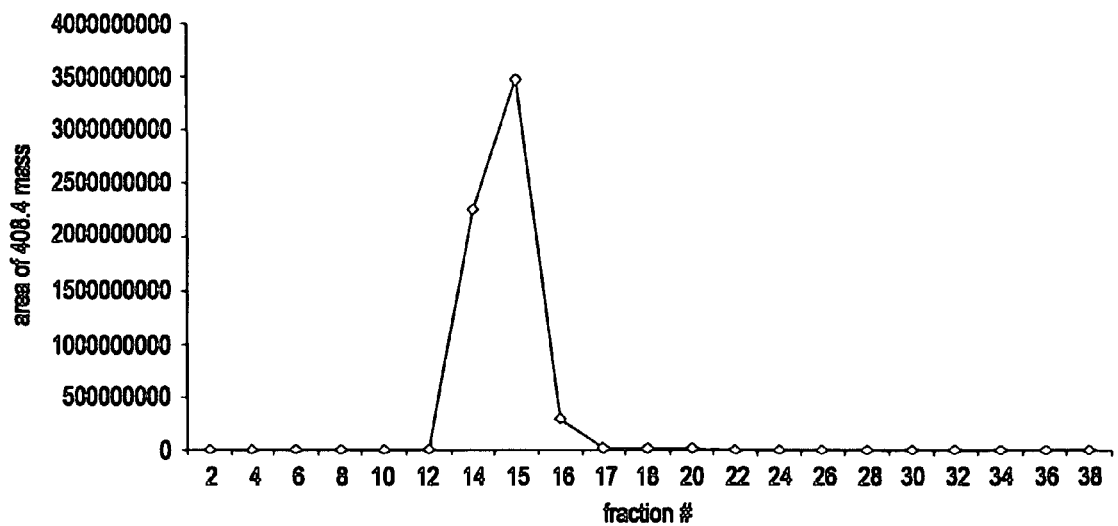
FIG. 10 illustrates the relative amounts of hexadecyl thiophosphocholine ("BRB-4") [M$^+$ H$^+$ 408.4] in column fractions of Example 2 in which the total area is plotted versus the fraction number.

The crude hexadecyl phosphocholine (BRB-1) of Example 1 was purified using a Diaion® HP-20S synthetic adsorbent polystyrene resin (Mitsubishi Chemical Corp.). The column fractions were then collected with water, methanol:water (1:1), and methanol. The collected fractions were analyzed using liquid chromatography/mass spectroscopy ("LC/MS") and the results are shown in FIG. 3. IR and NMR (proton, carbon and phosphorus) spectral analysis was performed and the results are shown in FIGS. 4-7. The structure of hexadecyl phosphocholine was confirmed by the spectral data shown in FIGS. 3-7. Similarly, tetradecyl phosphocholine (BRB-3) and hexadecyl thiophosphocholine (BRB-3) of Example 1 were purified as described above. The collected fractions were analyzed using liquid chromatography/mass spectroscopy ("LC/MS") and the results are shown in FIGS. 8-10. These figures confirm the structure of tetradecyl phosphocholine and hexadecyl thiophosphocholine.

EXAMPLE 3

The ability of the phosphocholine derivatives of Examples 1-2 to inhibit growth of *Candida albicans, Staphylococcus aureus, Lactobacillus acidophilus,* and *Gardnerella vaginale* was tested. Each phosphocholine derivative (at concentrations ranging from 0 to 500 micrograms per milliliter) was dissolved into a broth media and 6 wt. % ethanol. Thereafter, 0.1 milliliter of each solution was inoculated in 1.0 milliliter of a growth media containing the microorganism of interest. The growth media was TSB media for *Candida albicans* and *Staphylococcus aureus*, MRS broth for *Lactobacillus acidophilus*, and NYC-3 broth enriched proteose peptone for *Gardnerella vaginale*. The concentration of the microorganism in the growth media was $10^4$ colony forming units ("CFU") per milliliter.

Thereafter, the gross turbidity of the media was monitored at 24, 48, and 72 hours time intervals. Gross turbidity is an indicative of growth inhibition and is determined using visual determination or a spectrophotometer. The concentration of the phosphocholine derivative at which no turbidity is detected is designated as the "minimum inhibitory concentration." Phosphocholine derivatives having lower minimum inhibitory concentrations are generally considered to have better antimicrobial efficacy. The results are shown below in Table 2.

TABLE 2

Growth Inhibition by Phosphocholine Derivatives

| Name and Structure of Phosphocholine | Minimum Inhibitory Concentration (µg/ml) | | | |
|---|---|---|---|---|
| | S. aureus | L. acidophilus | G. vaginale | C. albicans |
| Hexadecyl phosphocholine | 125.00 | 125.00 | 31.25 | 15.60 |
| Tetradecyl Phosphocholine | 250.00 | 250.00 | 250.00 | 62.50 |
| Hexadecyl thiophosphocholine | 31.25 | 31.25 | 31.25 | 31.25 |

TABLE 2-continued

Growth Inhibition by Phosphocholine Derivatives

| Name and Structure of Phosphocholine | Minimum Inhibitory Concentration (μg/ml) | | | |
|---|---|---|---|---|
| | S. aureus | L. acidophilus | G. vaginale | C. albicans |
| 1,2-Dihexadecyl-rac-glycero-3-phosphocholine* | >500 | 500.00 | 250.00 | 250.00 |
| DL-α-lysophosphatidylcholine-r-o-hexadecyl* | 250.00 | 250.00 | 250.00 | 125.00 |

*obtained from Sigma-Aldrich Chemical Co. of St. Louis, Missouri.

As indicated, each of the phosphocholine derivatives exhibited the ability to inhibit microbial growth. Hexadecyl phosphocholine, for example, appeared to selectively inhibit the growth of C. albicans and G. vaginale over L. acidophilus and S. aureus.

EXAMPLE 4

Figure 11:
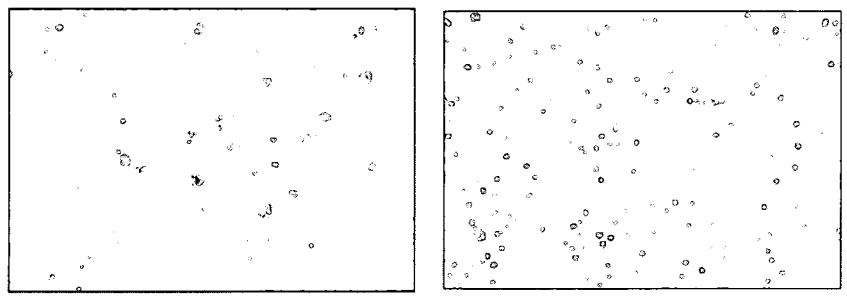
FIG. 11 shows phase microscopy images of the hexadecyl phosphocholine estradiol complex ("C-16PC:E2") for a neat sample (on the left) and a sample with 1× dilution in water (on the right) in Example 4.
Figure 12:
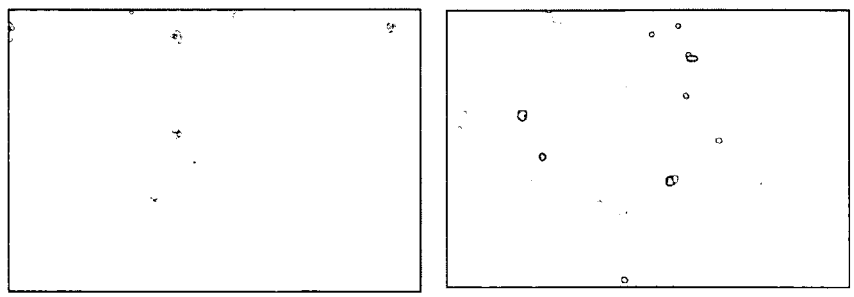
FIG. 12 shows phase microscopy images of the liquid hexadecyl phosphocholine ("C-16PC") (on the left) and liquid estradiol (on the right) in Example 4.

Liposome complexes were made with hexadecyl phosphocholine (C16PC) and estradiol (E2). Specifically, a solution of C16PC was formed by mixing C16PC (concentration of 26.8 milligrams per milliliter) with a solvent mixture. The solvent mixture contained methanol, propyl acetate, and methylene chloride in a ratio of 1:2.95:0.05, respectively. Similarly, a solution of E2 was formed by mixing E2 (concentration of 0.25 milligrams per milliliter) with a solvent mixture. The solvent mixture contained propyl acetate and methylene chloride in a ratio of 9.95:0.05, respectively. 400 microliters of the C16PC solution was then mixed with 400 microliters of the E2 solution and dried under a nitrogen stream. Upon rehydration of dried sample, the water suspension was centrifuged and a pellet was collected. Phase microscopic images were taken for the starting materials (C16PC and E2) (FIG. 12) and the resulting pellet (FIG. 11).

Figure 13:
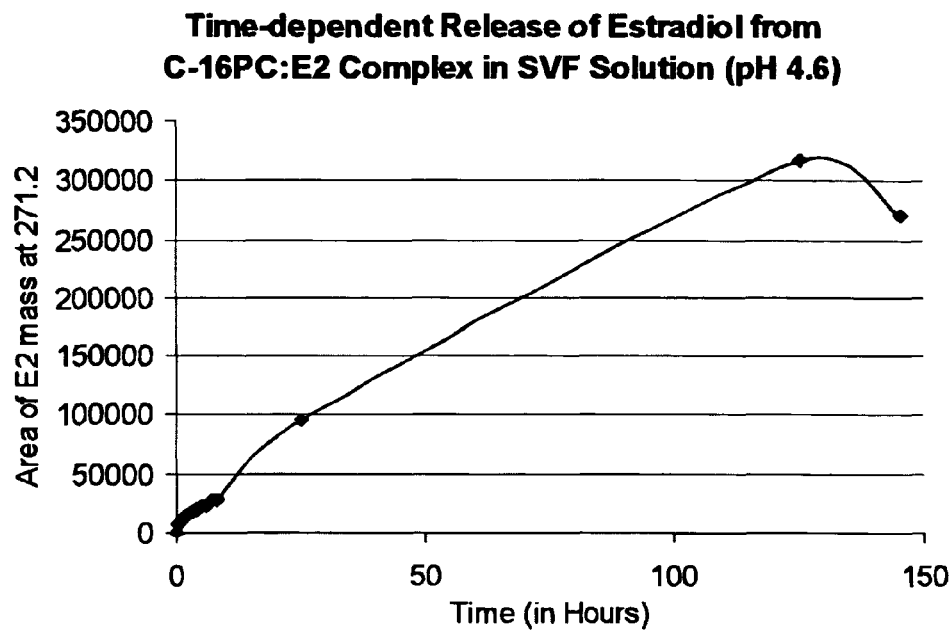
FIG. 13 is a graphical depiction of the time-dependent release of estradiol ("E2") from the hexadecyl phosphocholine/estradiol complex ("C-16PC:E2") in Example 4 in which the total area is plotted versus the release time for the range of times between 0 and 144 hours.
Figure 14:
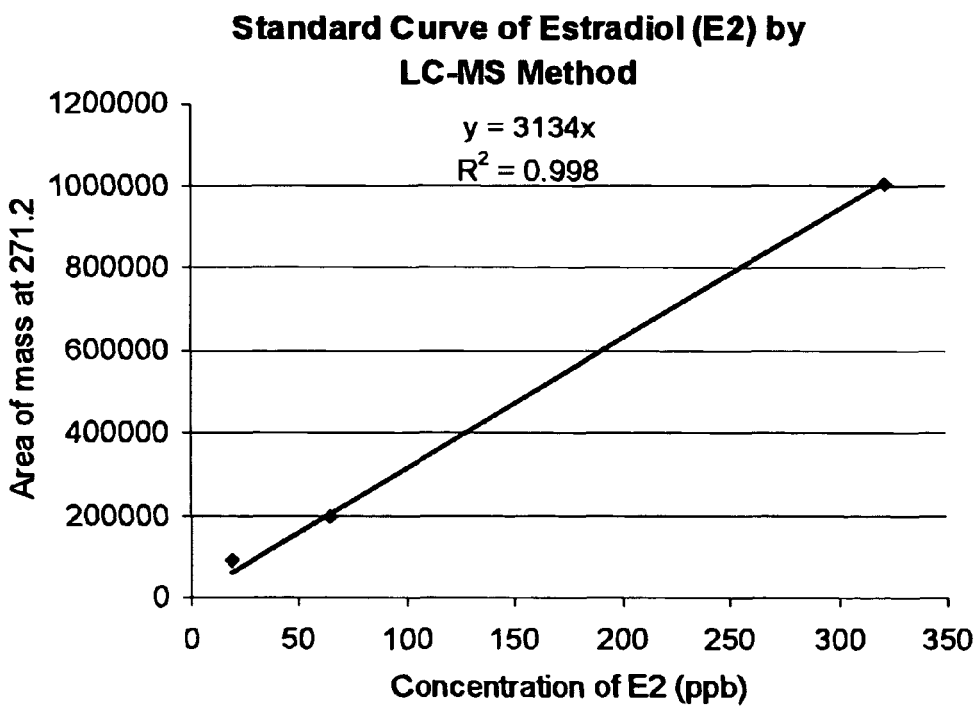
FIG. 14 is a graphical depiction of the standard curve generated for estradiol ("E2") using the LC-MS Method in Example 4 in which the total area is plotted versus the concentration of estradiol (parts per billion)
Figure 15:
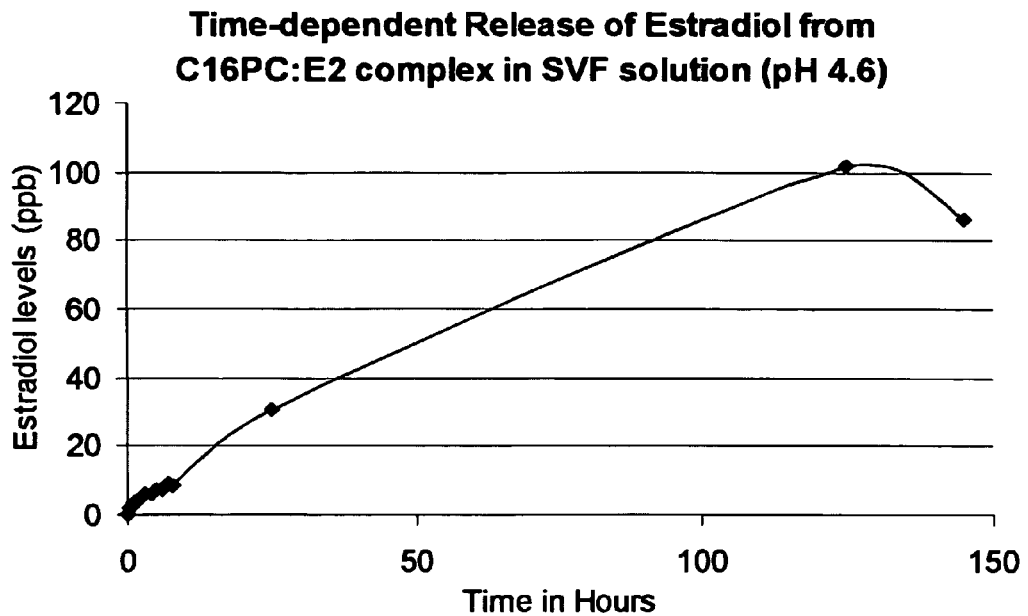
FIG. 15 is a graphical depiction of the time-dependent release of estradiol ("E2") from the hexadecyl phosphocholine/estradiol complex ("C-16PC:E2") in Example 4 in which the concentration of estradiol (parts per billion) is plotted versus the release time for the range of times between 0 and 144 hours.
Figure 16:
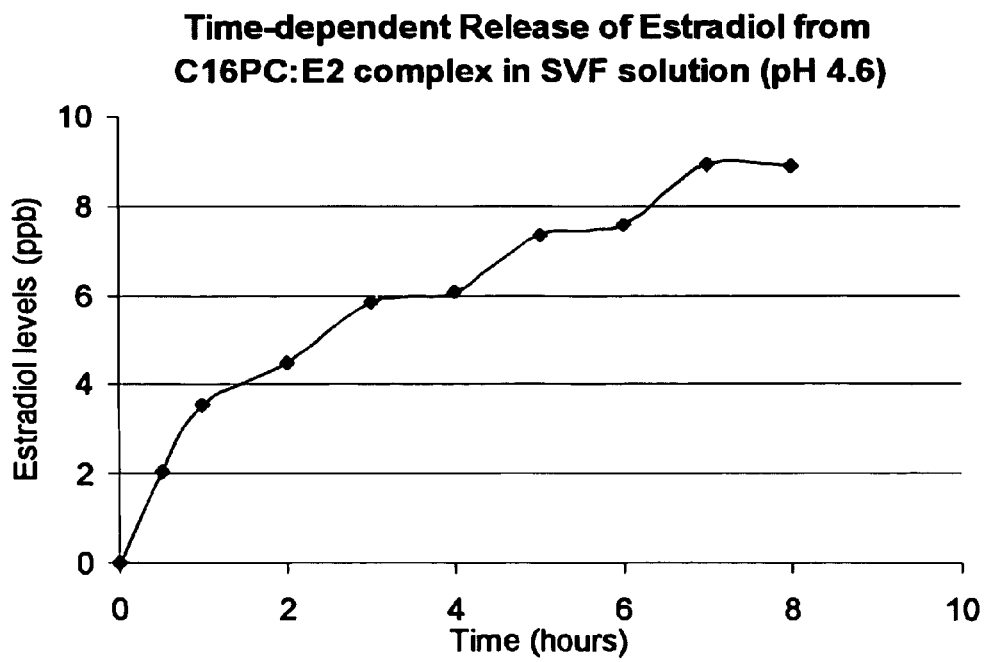
FIG. 16 is a graphical depiction of the time-dependent release of estradiol ("E2") from the hexadecyl phosphocholine/estradiol complex ("C-16PC:E2") in Example 4 in which the concentration of estradiol (parts per billion) is plotted versus the release time for the range of times between 0 and 8 hours.

Upon preparation of C16PC:E2 liposome complex, an in vitro release of estradiol was determined. Specifically, the C16PC:E2 liposome complex was placed in a mini-dialyzer (obtained from Pierce Biotechnology, Inc. under the name "MWCO 3500") and mixed with simulated vaginal fluid ("SVF") (pH of 4.6). The mini-dialyzer was placed in a glass vial containing the same SVF. At each time interval, an aliquot of SMF was taken and replaced with same amount of fresh SVF. The estradiol levels in the aliquots were determined by LC-MS and the results are shown in FIG. 14. As indicated, time-dependent release of estradiol was observed and the area of estradiol peak at 271.2 was plotted against the time of aliquot taken from vial and the results are shown in FIG. 13. The levels of estradiol released from the C16PC:E2 complex are shown with time in FIGS. 15-16.

EXAMPLE 5

Hexadecyl phosphocholine ("BRB-1") was studied for inhibition of Candida albicans (C. albicans), Staphylococcus aureus (S. aureus), and lactobacilli. The results are shown below in Tables 3-4. Tetradecyl phosphocholine ("BRB-3") was also studied for inhibition of C. albicans aureus, and lactobaccili. The results are shown in Table 5.

TABLE 3

Time-Dependent Inhibition of C. albicans and S. aureus

| System | BRB-1 Conc. (μg/ml) | Organism Count (CFU/ml) | | | | % Reduction | | | |
|---|---|---|---|---|---|---|---|---|---|
| | | 0 Hour | 1 Hour | 2 Hours | 4 Hours | 0 Hour | 1 Hour | 2 Hours | 4 Hours |
| C. albicans | 0 | $4.0 \times 10^5$ | $4.3 \times 10^5$ | $4.0 \times 10^5$ | $4.1 \times 10^5$ | — | NR | NR | 8.9 |
| C. albicans | 100 | $2.9 \times 10^5$ | $1.2 \times 10^5$ | $8.0 \times 10^2$ | $3.8 \times 10^2$ | 27.5 | 70.0 | 99.8 | 99.9 |
| C. albicans | 0 | $7.2 \times 10^5$ | $7.5 \times 10^5$ | $6.3 \times 10^5$ | $7.0 \times 10^5$ | — | NR | 12.5 | 2.8 |
| C. albicans | 10 | $8.4 \times 10^5$ | $2.3 \times 10^5$ | $2.1 \times 10^3$ | 50 | NR | 68.0 | 99.7 | 99.99 |
| S. aureus | 0 | $7.9 \times 10^4$ | $9.0 \times 10^4$ | $8.2 \times 10^4$ | $7.2 \times 10^4$ | — | NR | NR | 8.9 |
| S. aureus | 100 | $4.8 \times 10^4$ | $1.4 \times 10^2$ | 20 | ND | 39.2 | 99.8 | 99.97 | 99.99 |
| S. aureus | 0 | $6.5 \times 10^4$ | $6.4 \times 10^4$ | $7.2 \times 10^4$ | $6.0 \times 10^4$ | — | 1.5 | NR | 7.7 |
| S. aureus | 10 | $5.3 \times 10^4$ | $7.3 \times 10^2$ | 60 | ND | 18.5 | 98.9 | 99.91 | 99.98 |

NR—No reduction; ND—Not Detected

TABLE 4

Time-Dependent Inhibition of *L. acidophilus* (lactobacilli)

| BRB-1 Conc. (µg/ml) | Organism Count (CFU/ml) | | | Percent Reduction | | |
|---|---|---|---|---|---|---|
| | 0 Hour | 1 Hour | 6 Hours | 0 Hour | 1 Hour | 6 Hours |
| 0 | $2.2 \times 10^5$ | $2.1 \times 10^5$ | $2.1 \times 10^5$ | — | 4.5 | 4.5 |
| 100 | $1.5 \times 10^5$ | 70 | ND | 31.8 | 99.97 | 99.99 |
| 10 | $1.8 \times 10^5$ | 20 | ND | 18.2 | 99.99 | 99.99 |

| | Organism Count (CFU/ml) | | | | Percent Reduction | | | |
|---|---|---|---|---|---|---|---|---|
| | 0 Hour | 1 Hour | 2 Hours | 4 Hours | 0 Hour | 1 Hour | 2 Hours | 4 Hours |
| 0 | $7.5 \times 10^4$ | $8.2 \times 10^4$ | $7.1 \times 10^4$ | $7.1 \times 10^4$ | — | NR | 5.3 | 6.7 |
| 1 | $7.0 \times 10^4$ | $8.6 \times 10^4$ | $7.6 \times 10^4$ | $6.7 \times 10^4$ | 6.7 | NR | NR | 10.7 |

NR—No reduction; ND—Not detected

TABLE 5

Time-Dependent Inhibition of *C. albicans*, *S. aureus*, and *Lactobaccili*

| System | BRB-3 Conc. (µg/ml) | Organism Count (CFU/ml) | | | | Percent Reduction | | | |
|---|---|---|---|---|---|---|---|---|---|
| | | 0 Hour | 1 Hour | 2 Hours | 4 Hours | 0 Hour | 1 Hour | 2 Hours | 4 Hours |
| *C. albicans* | 0 | $7.3 \times 10^4$ | $7.2 \times 10^4$ | $8.2 \times 10^4$ | $7.7 \times 10^4$ | — | 1.4 | NR | NR |
| *C. albicans* | 10 | $7.1 \times 10^4$ | $5.8 \times 10^4$ | $5.1 \times 10^4$ | $3.5 \times 10^4$ | 2.7 | 20.5 | 30.1 | 52.0 |
| *C. albicans* | 0 | $1.0 \times 10^5$ | $8.8 \times 10^4$ | $8.0 \times 10^4$ | $7.8 \times 10^4$ | — | 12.0 | 20.0 | 22.0 |
| *C. albicans* | 100 | $7.4 \times 10^4$ | $5.7 \times 10^4$ | $4.9 \times 10^4$ | $5.4 \times 10^4$ | 26.0 | 43.0 | 51.0 | 46.0 |
| *S. aureus* | 0 | $1.2 \times 10^5$ | $1.1 \times 10^5$ | $1.1 \times 10^5$ | $1.2 \times 10^5$ | — | 8.3 | 8.3 | NR |
| *S. aureus* | 10 | $1.4 \times 10^5$ | $9.8 \times 10^4$ | $8.9 \times 10^4$ | $7.4 \times 10^4$ | NR | 18.3 | 25.8 | 38.3 |
| *S. aureus* | 0 | $1.4 \times 10^5$ | $1.6 \times 10^5$ | $1.5 \times 10^5$ | $1.3 \times 10^5$ | — | NR | NR | 7.1 |
| *S. aureus* | 100 | $1.3 \times 10^5$ | $2.9 \times 10^3$ | $1.1 \times 10^2$ | ND | 7.1 | 97.9 | 99.9 | 99.99 |
| *L. acidophilus* | 0 | $3.7 \times 10^5$ | $3.6 \times 10^5$ | $3.6 \times 10^5$ | $4.5 \times 10^5$ | — | 2.7 | 2.7 | NR |
| *L. acidophilus* | 10 | $3.1 \times 10^5$ | $2.9 \times 10^5$ | $2.4 \times 10^5$ | $2.3 \times 10^5$ | 16.2 | 21.6 | 35.1 | 37.8 |
| *L. acidophilus* | 0 | $3.9 \times 10^5$ | $3.8 \times 10^5$ | $3.8 \times 10^5$ | $3.0 \times 10^5$ | — | 2.6 | 2.6 | 23.1 |
| *L. acidophilus* | 100 | $4.5 \times 10^5$ | ND | — | — | 88.5 | 99.99 | — | — |

NR—No reduction; ND—Not detected

As indicated above, hexadecyl phosphocholine achieved particularly good inhibition of *C. albcans* and *S. aureus* in a time-dependent manner. Further, as indicated in Table 4 and 5, some inhibtion of lactobacilli with hexadecyl phosphocholine and tetradecyl phosphocholine occurred in this experiment. It is believed, however, that this result was due primarily to organism instability in the media conditions selected and the nature of the protocol employed (in comparison to example 3).

EXAMPLE 6

Figure 17:
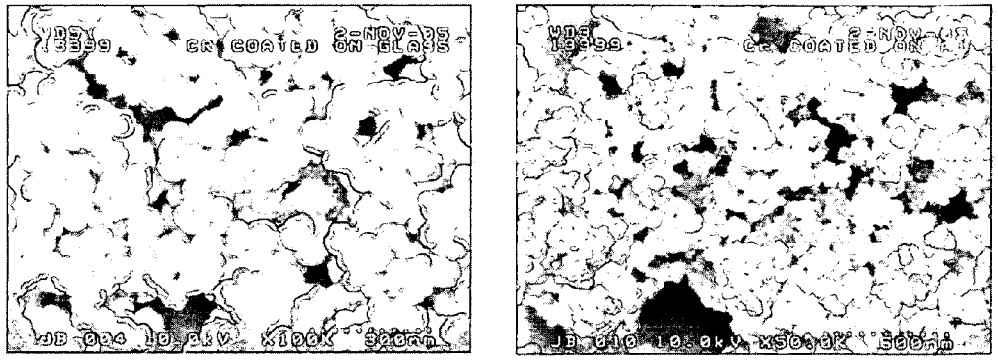
FIG. 17 shows field emission scanning electron microscopic images of C16PC:E2 particles (glass on the left and aluminum on the right) of Example 6.

Particles were made with hexadecyl phosphocholine (C16PC) and estradiol (E2). Specifically, a 10-milligram per milliliter stock solution of C16PC was made by mixing C16PC with a solvent mixture of tetrahydrofyran, propyl acetate and methal (300:1.6:0.4 ratio). Similarly, a stock solution of E2 was made by mixing E2 with a solvent mixture of tetrahydrofyran and propyl acetate (3:2.6 ratio). 100 microliters of the C16PC solution was mixed with 100 microliters of the E2 solution in a glass vial. Separrately, 6 milliliters of water was stirred in a 20-milliliter glass vial with a magnetic stir bar. After vigorous stirring of the water, 6- to 8-microliter aliquots of the C16PC/E2 mixture were added over a time period of 1 to 2 minutes. The solution was further stirred at the same rate for 5 minutes, and the derived particles were washed several times with water by centrifugation. The resulting C16PC:E2 particles were stored in water having a final volume of 1 milliliter. Field emission scanning electron microscopic images were then taken for the particles as shown in FIG. 17.

Figure 18:
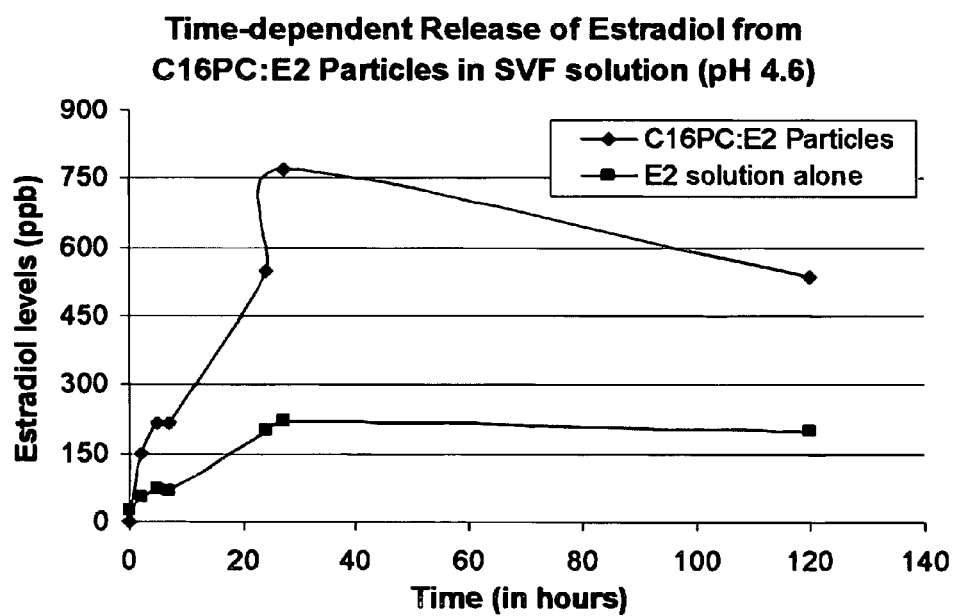
FIG. 18 is graphical depiction of time-dependent release of estradiol from C16PC:E2 particles in SVF solution (pH 4.6) for Example 6.

Upon preparation of the C16PC:E2 particles, an in vitro release of estradiol was determined. Specifically, 100 microliters of the C16PC:E2 particles were placed in a mini-dialyzer (obtained from Pierce Biotechnology, Inc. under the name "MWCO 3500") and mixed with 300 microliters of simulated vaginal fluid ("SVF") (pH of 4.6). The mini-dialyzer was placed in a glass vial containing the same SVF. In a parallel experiment, 200 microliters of a 50-microgram per milliliter stock solution of E2 was placed in a mini-dialyzer and mixed with 200 microliters of SVF. At each time interval, an aliquot of SVF was taken and replaced with same amount of fresh SVF. The estradiol levels in the aliquots were determined by liquid chromatography-mass spectrometry and the results are shown in FIG. 18.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A vaginal formulation comprising a dehydrated vesicle that consists of a phospholipid, a pharmaceutical agent, and a protecting sugar, the phospholipid being formed from an alkyl phosphocholine that comprises hexadecyl thiophosphocholine, tetradecyl phosphocholine, hexadecyl phosphocholine, docosanoyl phosphocholine, or a combination thereof, and the pharmaceutical agent including estradiol or an ester thereof.

2. The vaginal formulation of claim 1, wherein the alkyl phosphocholine is hexadecyl phosphocholine.

3. The vaginal formulation of claim 1, wherein phospholipids constitute from about 001 to about 1000 micrograms per milliliter of the vaginal formulation.

4. The vaginal formulation of claim 1, wherein phospholipids constitute from about 0.1 to about 100 micrograms per milliliter of the vaginal formulation.

5. The vaginal formulation of claim 1, wherein the pharmaceutical agent is a non-androgenic steroid selected from the group consisting of progestins, estrogens, and combinations thereof.

6. The vaginal formulation of claim 1, wherein the molar ratio of the phospholipid to the pharmaceutical agent is from about 3:1 to about 100:1.

7. A method for moisturizing and inhibiting the growth of microorganisms in a vagina of a female, the method comprising intravaginally administering a vaginal formulation so that the formulation is placed into contact with vaginal fluid in the vagina, the formulation comprising a vesicle that has been dehydrated in the presence of a protecting sugar, wherein the vesicle consists of the protecting sugar and a complex that inhibits the growth of *Candida albicans*, wherein the complex consists of a phospholipid and pharmaceutical agent, wherein the phospholipid is formed from an alkyl phosphocholine having the following structure:

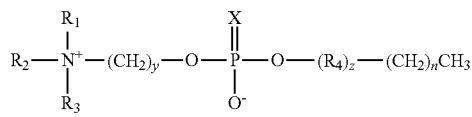

$R_1$, $R_2$, and $R_3$ are independently selected from the group consisting of hydrogen or $C_1$ to $C_6$ alkyl groups that are linear or branched, saturated or unsaturated, substituted or unsubstituted;

$R_4$ is an unsubstituted $C_1$ to $C_{40}$ alkyl group;
X is O, S, or NH;
y is from 1 to 10;
z is from 0 to 40; and
n is from 1 to 40,
wherein the pharmaceutical agent s released upon contacting the formulation with the vaginal fluid.

8. The method of claim 7, wherein n is from 4 to 24.

9. The method of claim 7, wherein the alkyl phosphocholine is selected from the group consisting of hexadecyl thiophosphocholine, tetradecyl phosphocholine, hexadecyl phosphocholine, docosanoyl phosphocholine, and combinations thereof.

10. The method of claim 7, wherein the alkyl phosphocholine is hexadecyl phosphocholine.

11. The method of claim 7, wherein phospholipids constitute from about 0.01 to about 1000 micrograms per milliliter of the formulation.

12. The method of claim 7, wherein phospholipids constitute from about 0.1 to about 100 micrograms per milliliter of the formulation.

13. The method of claim 7, wherein phospholipids constitute from about 0.2 to about 10 micrograms per milliliter of the formulation.

14. The method of claim 7, wherein phospholipids constitute from about 0.5 to about 5 micrograms per milliliter of the formulation.

15. The method of claim 7, wherein the complex also inhibits the growth of *Staphylococcus aureus*.

16. The method of claim 7, wherein the complex also inhibits the growth of *Gardnerella vaginale*.

17. The method of claim 7, wherein the complex inhibits the growth of *Candida albicans, Staphylococcus aureus, Gardnerella vaginale*, or combinations thereof without substantially inhibiting the growth of *Lactobacillus acidophilus*.

18. The method of claim 7, wherein the pharmaceutical agent is a non-androgenic steroid selected from the group consisting of progestins, estrogens, and combinations thereof.

19. The method of claim 18, wherein the pharmaceutical agent is estradiol or an ester thereof.

20. The method of claim 7, wherein the vesicle is a liposome or micelle.

21. The method of claim 7, wherein the pharmaceutical agent is controllably or sustainably delivered over a period of time of from about 2 to about 240 hours.

22. The method of claim 7, wherein the complex becomes hydrated upon administration.

\* \* \* \* \*

UNITED STATES PATENT AND TRADEMARK OFFICE
CERTIFICATE OF CORRECTION

PATENT NO.         : 8,703,179 B2
APPLICATION NO.    : 11/302992
DATED              : April 22, 2014
INVENTOR(S)        : RameshBabu Boga and Robert B. Johnson It is certified that error appears in the above-identified patent and that said Letters Patent is hereby corrected as shown below:

In the Claims

Claim 3 (column 21, line 10)

"…lipids constitute from about 001 to about 1000 micrograms…" should read --…lipids constitute from about 0.01 to about 1000 micrograms…--

Signed and Sealed this
Fifth Day of August, 2014

Michelle K. Lee
*Deputy Director of the United States Patent and Trademark Office*